United States Patent [19]
Van Broekhoven et al.

[11] Patent Number: 4,843,144
[45] Date of Patent: Jun. 27, 1989

[54] POLYMERIZATION OF CARBON MONOXIDE/OLEFIN WITH P LIGAND HAVING POLAR ARYL GROUP

[75] Inventors: Johannes A. M. Van Broekhoven; Richard L. Wife, both of CM Amsterdam, Netherlands

[73] Assignee: Shell Oil Company, Houston, Tex.

[21] Appl. No.: 89,375

[22] Filed: Aug. 26, 1987

[30] Foreign Application Priority Data

Aug. 26, 1986 [NL] Netherlands .......................... 8602164

[51] Int. Cl.$^4$ ............................................. C08G 67/02
[52] U.S. Cl. .................................................. 528/392
[58] Field of Search ......................................... 528/392

[56] References Cited

U.S. PATENT DOCUMENTS

| | | | |
|---|---|---|---|
| 2,495,286 | 1/1950 | Brubaker | 260/63 |
| 3,689,460 | 9/1972 | Nozaki | 260/63 |
| 3,694,412 | 9/1972 | Nozaki | 260/63 |
| 4,474,978 | 10/1984 | Drent | 560/24 |
| 4,634,793 | 1/1987 | Drent | 560/243 |

FOREIGN PATENT DOCUMENTS

| | | |
|---|---|---|
| 121965 | 8/1984 | European Pat. Off. . |
| 181014 | 5/1986 | European Pat. Off. . |
| 213671 | 3/1987 | European Pat. Off. . |
| 1081304 | 3/1965 | United Kingdom . |
| 2058074 | 8/1979 | United Kingdom . |

OTHER PUBLICATIONS

Kirk Othmer Encyclopedia of Chemical Technology, Second Edition, vol. 12, p. 132, 1967.

Primary Examiner—Harold D. Anderson
Attorney, Agent, or Firm—Dean F. Vance

[57] ABSTRACT

A polymerization process for the production of linear alternating polymers of carbon monoxide and at least one ethylenically unsaturated hydrocarbon employs a catalyst composition formed from a palladium compound, the anion of certain non-hydrohalogenic acids and certain bidentate ligands having ortho polar substitution within at least one monovalent phosphorus substituent and optionally a quinone. The polymer product is obtained in the form of globules.

10 Claims, No Drawings

POLYMERIZATION OF CARBON MONOXIDE/OLEFIN WITH P LIGAND HAVING POLAR ARYL GROUP

This invention relates to an improved process for the production of polymers of carbon monoxide and ethylenically unsaturated hydrocarbon and to certain novel catalyst compositions formed from certain Group VIII metal compounds, anions of certain acids, and phosphorus bidentate ligands, which compositions are useful in the improved process.

The polymerization of carbon monoxide and at least one ethylenically unsaturated hydrocarbon is known to provide linear alternating polymers of carbon monoxide and hydrocarbon which are known as polyketones. For example the polymerization product of carbon monoxide and ethylene is a linear alternating polymer of units of the formula $-CO(C_2H_4)-$. Polymerization is typically conducted in the presence of a catalyst composition prepared from certain Group VIII metals such as palladium, an anion of a non-hydrohalogenic acid having a pKa less than about 6, a bidentate ligand of phosphorus and optionally, in some instances, a fourth catalyst component depending upon the particular catalyst composition.

In the production of polyketone polymers, reaction rate and product molecular weight are important considerations. From a manufacturing efficiency standpoint, it is desirable to have a rapid reaction rate. From a product point of view, polymers of higher molecular weight generally exhibit the more desirable properties. Increase in reaction rate is typically effected by increasing the reaction temperature. Unfortunately a rise in reaction temperature will frequently result in a decrease of product molecular weight. Reaction conditions are generally established to provide product of desirable molecular weight and any undesirable reaction rates must simply be tolerated.

A second product consideration relates to the morphology of the resulting polymer particles. Where rather small, fluffy particles of polymer product are obtained, it is relatively difficult to separate, purify and process the product. Product recovery and processing would be easier if the polymer product comprised relatively large globular particles.

It is desirable to provide a process for the production of polyketones which incorporates a relatively rapid reaction rate and produces relatively high molecular weight polymer in the form of globular particles.

SUMMARY OF THE INVENTION

The process of the invention is an improved process for polymerizing carbon monoxide and at least one ethylenically unsaturated hydrocarbon in the presence of a catalyst composition prepared by reacting a palladium compound, the anion of a non-hydrohalogenic acid having a pKa less than 6 and a bidentate phosphorus ligand in which the monovalent substituents of the phosphorus are aryl and at least one of the substituents incorporates polar substitution in a position ortho to the phosphorus. Optionally, certain quinones may additionally be employed. The invention also contemplates the novel catalyst compositions useful in the improved process.

DESCRIPTION OF THE INVENTION

The phosphorus bidentate ligand of the invention has the formula $R^1R^2\text{-P-R-P-}R^3R^4$ wherein $R^1$, $R^2$, $R^3$ and $R^4$ independently are aryl groups of from 6 to 20 carbon atoms inclusive, preferably from 6 to 10 carbon atoms inclusive, and are hydrocarbon or substituted hydrocarbon wherein any substituents are polar, with the provision that at least one $R^1$, $R^2$, $R^3$ and $R^4$ is substituted with a polar group in a position ortho to the phosphorus. R is a divalent bridging group of from 1 to 20 carbon atoms inclusive, preferably from 1 to 10 carbon atoms, and has from 2 to 4 inclusive, preferably 3, carbon atoms in the phosphorus-phosphorus bridge. R is preferably hydrocarbyl but substituted hydrocarbyl R groups are also satisfactory, particularly when substituents are of the formula $-PR^1R^2$. Ligands containing the group $-CH_2-CH_2-CH_2-$ as the divalent R group are preferred.

A variety of polar substituents for the $R^1$, $R^2$, $R^3$ and $R^4$ groups are satisfactory, provided that the polar substituents are inert to the polymerization reaction. Illustrative of suitable polar substituents are $R^5-O-$, $R^5-S-$, $R^5-CO-$, $R^5-CO-NH$, $R^5R^6N-$, $R^5-CO_2$, $R^5R^6N-CO-$ and $R^5CO-NR^6-$ wherein $R^5$ and $R^6$ independently are hydrocarbyl groups of from 1 to 10 carbon atoms. The polar groups alkoxy, alkylthio and alkylcarboxy represent a preferred class of polar substituents with alkoxy, e.g., methoxy, ethoxy, butyloxy and pentyloxy being particularly preferred. Especially good results are obtained with methoxy polar substituents.

To obtain the advantages of the process of the invention it is required that at least one of $R^1$, $R^2$, $R^3$ and $R^4$ be substituted with a polar group in a position ortho to the phosphorus. More than one of the $R^1$, $R^2$, $R^3$ and $R^4$ substituents is suitably ortho substituted with a polar group and, largely for ease of production, the bidentate ligands wherein each of $R^1$, $R^2$, $R^3$ and $R^4$ is substituted in an ortho position relative to the phosphorus with the same polar group are particularly preferred. The $R^1$, $R^2$, $R^3$ and $R^4$ groups are suitably substituted with additional polar groups if desired, preferably in positions ortho or para to the phosphorus but such $R^1$, $R^2$, $R^3$ and $R^4$ groups substituted solely in one ortho position are preferred.

Illustrative of bidentate phosphorus ligand are 1,3-bis[di(2-methoxyphenyl)phosphino]propane, 1,3-bis[di(2,4-dimethoxyphenyl)phosphino]propane, 1,3-bis[di(2-ethoxyphenyl) phosphino]propane, 1,3-bis[di(2,6-dimethoxyphenyl)phosphino]propane and 1,3-bis[di(2,4,6-trimethoxyphenyl)phosphino]propane. The bidentate phosphorus ligand is utilized in an amount from about 0.1 mol to about 2 mol per mol of palladium compound, preferably from about 0.75 mol to about 1.5 mol per mol of palladium compound.

The palladium compound is provided in the form of a salt, particularly the salt of a carboxylic acid such as palladium acetate or palladium propionate. Palladium acetate is generally preferred. The anion employed is an anion of a non-hydrohalogenic acid having a pKa less than about 6, preferably less than 2, as determined in aqueous solution at 18° C. The acid is preferably an oxygen-containing acid and is inorganic such as sulfuric acid or perchloric acid or is organic such as the carboxylic acids trifluoroacete acid and trichloroacetic acid or the sulfonic acids such as methanesulfonic acid and p-toluene-sulfonic acid. The acids trifluoroacetic acid and para-toluenesulfonic acid area preferred class.

The anion of the acid is introduced as the acid or in the form of a metal salt of the acid. The salt is a salt of a transition metal, i.e., a metal of Group I B to Group VII B of the Periodic Table of Elements, or is the salt of a non-transition metal, i.e., a metal of Group IA to Group VA of the Periodic Table of Elements. In general, transition metal salts are preferred when the anion is provided in the form of a salt and particularly copper salts. In an alternate modification, the palladium compound and the anion are jointly provided as by utilization of $Pd(CH_3CN)_2(OSO_2—C_6H_4—CH_3)_2$ prepared by reaction of palladium chloride and silver para-toluenesulfonate in acetonitrile or by reaction of palladium acetate and para-toluene-sulfonic acid in acetonitrile.

In an optional but preferred embodiment of the invention, the catalyst composition incorporates a quinone. A variety of quinones is useful when a quinone is utilized, particularly 1,4-quinones. The quinone is a hydrocarbyl quinone or is substituted with non-hydrocarbyl substituents and is mono-cyclic, such as 1,4-benzoquinone or is polycyclic such as 1,4-naphthaquinone or an anthraquinone. Benzoquinones are preferred and particularly 1,4-benzoquinone. The presence or absence of a quinone is optional and up to 10000 mols of quinone per gram atom of palladium are satisfactory, with up to 5000 mols of quinone per gram atom of palladium compound being preferred.

The catalyst compositions are employed in the polymerization of carbon monoxide and at least one ethylenically unsaturated hydrocarbon. In the case of the hydrocarbon, polymerization takes place through the ethylenic linkage to produce a linear alternating polymer having units of the formula —CO(hydrocarbon moiety)—. Suitable ethylenically unsaturated hydrocarbons have 2 to 20 carbon atoms inclusive, preferably 2 to 10 carbon atoms inclusive, and include aliphatic olefins, particularly ethylene and other α-olefins such as propylene, butene-1, 4-methyl-pentene-1, hexene-1 and dodecene-1. Also suitable are aryl-substituted ethylenes such as styrene, p-methylstyrene and p-ethylstyrene. Ethylene is a preferred unsaturated hydrocarbon, particularly when copolymers of carbon monoxide and a single ethylenically unsaturated hydrocarbon are desired. When a second ethylenically unsaturated hydrocarbon is employed in the production of terpolymers with carbon monoxide and ethylene, propylene is preferred as the second hydrocarbon. Amounts of second hydrocarbon when employed are up to about 0.01 mol per mol of first hydrocarbon, preferably up to about 0.025 mol per mol of first hydrocarbon.

In the mixture of carbon monoxide and ethylenically unsaturated hydrocarbon to be polymerized, ratios (by mol) of carbon monoxide to hydrocarbon from about 10:1 to about 1:5 are suitable with ratios from about 5:1 to about 1:2 being preferred.

The polymerization process is conducted by contacting carbon monoxide and at least one ethylenically unsaturated hydrocarbon in the presence of a catalytic amount of the catalyst composition under polymerization conditions. In one modification, the polymerization is conducted in the presence of a liquid diluent. Preferred diluents are alcohols, particularly the lower alkanols of up to 6 carbon atoms such as methanol and ethanol. In an alternate modification the process is conducted in the gas phase in the substantial absence of a liquid phase.

The optimum quantity of catalyst composition to be employed will vary. For each mol of ethylenically unsaturated hydrocarbon to be polymerized, from about $1\times10^{-7}$ to about $1\times10^{-3}$ gram atom of palladium are employed, preferably from about $1\times10^{-6}$ to about $1\times10^{-4}$ g atom atom of palladium.

Useful polymerization temperatures are from about 20° C. to about 200° C., preferably from about 30° C. to about 150° C., with reaction pressures varying from about 1 bar to about 200 bar, preferably from about 20 bar to about 100 bar. The method of contacting polymerizable reactants and catalyst composition is not critical and conventional methods such as shaking and stirring are satisfactory. Subsequent to reaction, the polymer product is recovered by conventional methods such as filtration or decantation, made particularly useful by the advantageous morphology of the polymer product. On occasion the polymer contains residues of the catalyst composition which may be removed, if desired, by mixing the residue-containing polymer with a solvent selective for the catalyst residue.

In determining the molecular weight of a polymer product, it is useful to determine the intrinsic viscosity since in general the intrinsic viscosity increases as the molecular weight of the polymer increases. In order to determine the intrinsic viscosity of a polymer of the type prepared according to the invention, four solutions of differing concentration are prepared by dissolving the polymer in m-cresol at 100° C. The viscosity at 100° C. of each of these solutions relative to m-cresol at 100° C. is determined in a viscometer. When $T_o$ represents the efflux time of m-cresol and $T_p$ the efflux time of the polymer solution, the relative viscosity ($\eta_{rel}$) is determined by $\eta_{rel}=To/Tp$. The inherent viscosity ($\eta_{inh}$) is calculated by the formula $\eta_{inh}=\ln \eta_{rel}/c$ where c represents the polymer concentration as grams of polymer per 100 grams of solution. Plotting the $\eta_{inh}$ of each of the four polymer solutions against the corresponding c value and extrapolation to c=o leads to the intrinsic viscosity which will hereafter be referred to by the alternate designation Limiting Viscosity Number, LVN, which is recommended by the International Union of Pure and Applied Chemistry.

The polymer products of the invention are globular particles of from about 0.05 mm to about 5 mm in diameter and particularly from about 0.2 mm to about 3 mm in diameter, in contrast with rather irregular and fluffy particles produced by other methods. This favorable morphology results in decided advantages in recovery and processing.

The polymer products, being of relatively high molecular weight, have known utility as premium thermoplastics for fibers, film and molding or blowing applications. They are particularly useful for applications in the auto industry, for the manufacture of packaging materials for food and drink and for the manufacture of cables and other building and construction applications. The polymers are utilized as such or in blends with other thermoplastics.

The invention is further illustrated by the following Comparative Examples (not of the invention) and Illustrative Embodiments.

COMPARATIVE EXAMPLE I

A carbon monoxide/ethylene copolymer was prepared by introducing 250 ml of methanol into a mechanically stirred autoclave of 300 ml capacity. Any air present was removed by charging the autoclave three times with carbon monoxide to a pressure of 50 bar and then releasing the pressure. After the autoclave contents had been heated to 65° C., a 1:1 by mol mixture of carbon monoxide and ethylene was introduced until a pressure of 55 bar was reached. A catalyst solution was then introduced into the autoclave comprising 6 ml of methanol, 0.01 mmol of palladium acetate, 0.02 mmol of p-toluenesulfonic acid and 0.012 mmol of 1,3-bis-(diphenylphosphino)propane. The pressure was maintained at 55 bar through addition of the equimolar carbon-monoxide/ethylene mixture. After 3 hours, the polymerization was stopped by cooling the reaction mixture to room temperature and releasing the pressure.

The copolymer was removed by filtration, washed with methanol and dried at 70° C. The copolymer product, 6.0g, had an LVN of 1.0 dl/g. The calculated reaction rate was 2.0 kg of copolymer/g Pd/hr.

COMPARATIVE EXAMPLE II

The procedure of Comparative Example I was repeated except that the reaction temperature was 85° C. and the reaction time was 2.5 hours. The copolymer product, 15.25 g, had a LVN of 0.6 dl/g and was produced at a calculated reaction rate of 6.1 kg of copolymer/g Pd/hr.

ILLUSTRATIVE EMBODIMENT I

The procedure of Comparative Example I was repeated, except that the reaction temperature was 71° C. instead of 65° C., the reaction time was 2.5 hours instead of 3 hours and the catalyst composition contained 1,3-bis[di(2-methoxyphenyl)phosphino]propane instead of 1,3-bis(diphenylphosphino)propane. The copolymer product, 3.25 g, had an LVN of 4.0 dl/g and was produced at the calculated rate of 1.3 kg of copolymer/g Pd/hr.

ILLUSTRATIVE EMBODIMENT II

The procedure of Comparative Example I was repeated except that the reaction temperature was 85° C. instead of 65° C. and the catalyst composition contained 1,3-bis[di(2-methoxyphenyl)phosphino]propane instead of 1,3-bis(diphenylphosphino)propane. 6.0 G of copolymer was obtained having a LVN of 2.9 dl/g. The calculated reaction rate was 2.0 kg of copolymer/g Pd/hr.

ILLUSTRATIVE EMBODIMENT III

The procedure of Illustrative Embodiment II was repeated except that the reaction temperature was 97° C. The polymer product, 13.5 g, had a LVN of 1.0 dl/g and was produced at a calculated rate of 4.5 kg of copolymer/gPd/hr.

ILLUSTRATIVE EMBODIMENT IV

The procedure of Illustrative Embodiment III was repeated except that the catalyst solution additionally contained 2 mmol of 1,4-benzoquinone. A product of 36.6 g was produced at a rate of 12.2 kg of copolymer/g Pd/hr with an LVN of 1.0 dl/g.

ILLUSTRATIVE EMBODIMENT V

A procedure was carried out by substantially the method of Comparative Example I, except that
(a) the reactor contained 150 ml of methanol instead of 250 ml,
(b) the reaction temperature was 95° C. instead of 65° C.,
(c) the catalyst solution consisted of 6 ml of methanol, 0.02 mmol of palladium acetate, 0.4 mmol of trifluoroacetic acid, 0.024 ml of 1,3-bis[di(2,4-dimethoxyphenyl)phosphino]propane and 2 mmol of 1,4-benzoquinone, and
(d) the reaction time was 2 hours instead of 3 hours.
The copolymer product, 16.2 g, had an LVN of 1.4 dl/g and was produced at the calculated reaction rate of 4.1 kg of copolymer/g Pd/hr.

COMPARATIVE EXAMPLE III

A carbon monoxide/ethylene/propylene terpolymer was produced by charging 180 ml of methanol to a mechanically stirred autoclave of 300 ml capacity. Any air present was expelled by charging the autoclave three times with carbon monoxide until a pressure of 50 bar was reached and then releasing the pressure. After 30 ml of liquid propylene was introduced into the reactor and the temperature of the contents raised to 55° C., a 1:1 mixture (by mol) of carbon monoxide and ethylene was introduced until a pressure of 56 bar was reached. A catalyst solution was then added which comprised 6 ml of methanol, 0.01 mmol of palladium acetate, 0.2 mmol of trifluoroacetic acid and 0.012 mmol of 1,3-bis(diphenylphosphino)propane. The pressure was maintained at 56 bar through addition of an equimolar mixture of carbon monoxide and ethylene. After 10 hours the reaction was terminated by cooling the reaction mixture to room temperature and releasing the pressure. The terpolymer was removed by filtration, washed with methanol and dried at 70° C. The terpolymer product, 12.6 g, had a melting point of 221° C. and an LVN of 1.0 dl/g. The calculated reaction rate was 1.2 kg of terpolymer/g Pd/hr.

COMPARATIVE EXAMPLE IV

The procedure of Comparative Example III was repeated except that the reaction temperature was 40° C. instead of 55° C. The polymer product, 2 g of terpolymer, had a melting point of 218° C. and a LVN of 2.4 dl/g. The calculated reaction rate was 0.2 g of terpolymer/g Pd/hr.

ILLUSTRATIVE EMBODIMENT VI

The procedure of Comparative Example III was repeated except that the reaction temperature was 85° C. instead of 55° C., the reaction time was 4 hours instead of 10 hours, and the catalyst solution contained 1,3-bis[di(2-methoxyphenyl)phosphino]propane instead of 1,3-bis(diphenylphosphino)propane. 22 G of terpolymer was obtained having a melting point of 220° C. and an LVN of 1.0 dl/g. The calculated reaction rate was 5.5 kg of terpolymer/g Pd/hr.

ILLUSTRATIVE EMBODIMENT VII

The procedure of Illustrative Embodiment VI was repeated except that the reaction temperature was 75° C. instead of 85° C. and the catalyst solution additionally contained 2 mmol of 1,4-benzoquinone. There was obtained 15.2 g of terpolymer having a melting point of 223° C. and an LVN of 2.4 dl/g. The calculated reaction rate was 3.8 kg of terpolymer/g Pd/hr.

ILLUSTRATIVE EMBODIMENT IX

The procedure of Comparative Example III was repeated except that the reaction temperature was 75° C. instead of 55° C., the reaction time was 2 hours instead of 10 hours, the catalyst solution contained 1,3- bis[di-(2-methoxyphenyl)phosphino]propane instead of 1,3-bis(diphenylphosphino)propane and 0.02 mmol of copper para-tosylate (para-toluenesulfonate) instead of the trifluoracetic acid, and additionally 2 mmol of 1,4-benzoquinone. The terpolymer product, 22.6 g, had a melting point of 217° C. and an LVN of 0.8 dl/g. The calculated reaction rate was 11.3 kg of terpolymer/g Pd/hr.

ILLUSTRATIVE EMBODIMENT X

The procedure of Comparative Example III was substantially repeated to prepare a terpolymer of carbon monoxide, ethylene and octene-1. The procedural differences were that 83 ml of octene-1 were used instead of 30 ml of propylene, the reaction time was 2 hours instead of 10 hours, the reaction temperature was 76° C. instead of 55° C., the reaction pressure was 54 bar instead of 56 bar, and the catalyst solution contained 1,3-bis[di(2-methoxyphenyl)phosphine]propane instead of 1,3-bis(diphenylphosphino)propane and additionally contained 2 mmol of 1,4-benzoquinone. The terpolymer product, 13.8 g, had a melting point of 230° C. and an LVN of 1.1 dl/g. The calculated reaction rate was 6.9 kg of terpolymer/g Pd/hr.

ILLUSTRATIVE EMBODIMENT XI

The procedure of Illustrative Embodiment IX was followed to prepare a carbon monoxide/ethylene/dodecene-1 terpolymer. The procedural differences were that 83 ml of dodecene-1 were used instead of 83 ml of octene-1 and the reaction temperature was 70° C. instead of 76° C. The terpolymer product, 10.4 g, had a melting point of 240° C. and an LVN of 2.1 dl/g. The calculated reaction rate was 2.6 kg of terpolymer/g Pd/hr.

ILLUSTRATIVE EMBODIMENT XII

The procedure of Comparative Example III was employed to prepare a carbon monoxide/ethylene/octene-1 terpolymer, the differences being that
(a) 83 ml of octene-1 were used instead of 30 ml of propylene,
(b) 150 ml of methanol were charged to the autoclave instead of 180 ml
(c) the reaction temperature was 75° C. instead of 55° C.,
(d) the reaction pressure was 50 bar instead of 56 bar,
(e) a catalyst solution was employed which comprised 0.02 mmol of palladium acetate, 0.4 mmol of trifluoroacetic acid, 0.024 mmol of 1,3-bis[di-2,4-methoxyphenyl)phosphine]propane and 2 mmol of 1,4-benzoquinone, and
(f) the reaction time was 2.5 hours instead of 10 hours.

The terpolymer product, 20 g, had a melting point of 240° C. and an LVN of 2.2 dl/g and was produced at a calculated reaction rate of 4 kg of terpolymer/g Pd/hr.

With the aid of $^{13}$C-NMR analysis it was established that the carbon monoxide/ethylene copolymers had a linear structure of units of the formula —CO($C_2H_4$)—. All carbon monoxide/ethylene copolymers had a melting point of 257° C. It was also established through $^{13}$C-NMR analysis that the terpolymers prepared above from carbon monoxide, ethylene and propylene, octene-1 or dodecene-1 had linear structures containing units of the formula —CO($C_2H_4$)—and, randomly distributed through the terpolymer, units of the formula —CO($C_3H_6$)—, —CO($C_8H_{16}$)— and —CO($C_{12}H_{24}$)—respectively. The products of the Illustrative Examples are globular in form.

What is claimed is:

1. In the process of producing linear alternating polymers by contacting under polymerization conditions carbon monoxide and at least one ethylenically unsaturated hydrocarbon in the presence of a catalyst composition formed from a palladium compound, an anion of a non-hydrohalogenic acid having a pKa less than 2 and bidentate phosphorus ligand, the improvement wherein the bidentate phosphorus ligand has the formula $R^1R^2$-P-R-P-$R^3R^4$ wherein $R^1$, $R^2$, $R^3$ and $R^4$ independently are aryl groups of from 6 to 20 carbon atoms inclusive and R is a divalent bridging group of from 1 to 20 carbon atoms inclusive and of from 2 to 4 carbon atoms inclusive in the phosphorus-phosphorus bridge, with the provision that at least one of $R^1$, $R^2$, $R^3$ and $R^4$ is substituted with a polar group in a position ortho to the phosphorus.

2. The process of claim 1 wherein $R^1$, $R^2$, $R^3$ and $R^4$ are substituted hydrocarbyl wherein the substituents are polar and R is hydrocarbyl with three carbons in the phosphorus-phosphorus bridge.

3. The process of claim 2 wherein $R^1$, $R^2$, $R^3$ and $R^4$ independently have from 6 to 10 carbon atoms inclusive and the polar sustituents are alkoxy, alkylthio or alkylcarboxy.

4. The process of claim 3 wherein R is —$CH_2$—$CH_2$—$CH_2$—.

5. The process of claim 4 wherein $R^1$, $R^2$, $R^3$ and $R^4$ are phenyl substituted with alkoxy.

6. The process of claim 5 wherein the alkoxy is methoxy.

7. The process of claim 5 wherein the alkoxy is ethoxy.

8. The process of claim 5 wherein $R^1$, $R^2$, $R^3$ and $R^4$ are 2-methoxyphenyl.

9. The process of claim 5 wherein $R^1$, $R^2$, $R^3$ and $R^4$ are 2,4-dimethoxyphenyl.

10. In the process of producing linear alternating polymers by contacting under polymerization conditions carbon monoxide and at least one ethylenically unsaturated hydrocarbon in the presence of a catalyst composition formed from a palladium compound, an anion of non-hydrohalogenic acid having a pKa less than 2 and a bidentate phosphorus ligand, the improvement wherein the bidentate phosphorus ligand has the formula $R^1R^2$-P-R-P-$R^3R^4$ wherein $R^1$, $R^2$, $R^3$ and $R^4$ independently are aryl groups of from 6 to 20 carbon atoms inclusive and R is a divalent bridging group of up to 20 carbon atoms inclusive and from 2 to 4 carbon atoms inclusive in the phosphorus-phosphorus bridge, with the proviso that at least one of the $R^1$, $R^2$, $R^3$ and $R^4$ is substituted with a polar group in a position ortho to the phosphorus, and recovering the linear alternating polymer as globular particles of from about 0.05 mm to about 5 mm in diameter.

* * * * *